(12) United States Patent
Ouchi

(10) Patent No.: US 6,423,060 B1
(45) Date of Patent: Jul. 23, 2002

(54) HIGH-FREQUENCY INSTRUMENT FOR ENDOSCOPE

(75) Inventor: Teruo Ouchi, Saitama (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/456,547

(22) Filed: Dec. 8, 1999

(30) Foreign Application Priority Data

Jan. 7, 1999 (JP) .......................................... 11-001738
Jan. 7, 1999 (JP) .......................................... 11-001739

(51) Int. Cl.$^7$ .............................................. A61B 18/18
(52) U.S. Cl. .................. 606/41; 46/45; 46/49
(58) Field of Search ............................... 606/41, 45, 46, 606/47, 48, 49, 50

(56) References Cited

U.S. PATENT DOCUMENTS 5,261,906 A * 11/1993 Pennino et al. ............... 606/46
5,462,553 A * 10/1995 Dolgin ........................ 606/113
5,540,683 A * 7/1996 Ichikawa et al. .............. 606/40

FOREIGN PATENT DOCUMENTS

| JP | 60-31684 | 9/1985 |
| JP | 61-4326 | 2/1986 |
| JP | 63-65852 | 3/1988 |

* cited by examiner

*Primary Examiner*—R. Kearney
(74) *Attorney, Agent, or Firm*—Greenblum & Bernstein, P.L.C.

(57) ABSTRACT

A high-frequency instrument for an endoscope including an electrically insulating sheath having a high-frequency electrode provided at the distal end thereof. A operating part is connected to the proximal end of the sheath. The operating part has an electrically conducting member electrically connected to the high-frequency electrode. An electrically insulating member covers the whole outer surface of the electrically conducting member. An electrically conductive rod electrically connected to the electrode may be inserted in the sheath. An electrically insulating member covers the whole outer surface of the rod except a portion thereof that is engageable with an operating member.

4 Claims, 5 Drawing Sheets

HIGH-FREQUENCY INSTRUMENT FOR ENDOSCOPE

BACKGROUND OF THE INVENTION

The present disclosure relates to subject matter contained in Japanese Patent Application No. 11-1738 (filed on Jan. 7, 1999) and Japanese Patent Application No. 11-1739 (filed on Jan. 7, 1999), which are expressly incorporated herein by reference in their entireties.

1. Field of the Invention

The present invention relates to a high-frequency instrument that is removably inserted into an instrument-inserting channel of an endoscope and used to carry out a treatment by passing a high-frequency electric current therethrough.

2. Description of the Prior Art

In general, a high-frequency instrument for an endoscope has a high-frequency electrode secured to the distal end of a sheath that is removably inserted into an instrument-inserting channel of an endoscope. A operating part is connected to the proximal end of the sheath, and an electrically conducting member that is electrically connected to the high-frequency electrode is disposed in the operating part.

A high-frequency treatment using an endoscope is performed as follows. A patient plate is set in close contact with the patient's body, and the high-frequency electrode, which is provided at the distal end of the sheath, is touched to the affected part to pass a high-frequency electric current between the two electrodes.

The electric current flows through a circuit formed between the patient's body and a high-frequency power supply. Therefore, the doctor is not included in the high-frequency circuit if touching the conducting path of the instrument. As in the case of a bird perching on an electric line without getting an electric shock, the doctor can touch the conducting path without causing an accident.

However, if the doctor touches the conducting path of the instrument while being in contact with the patient's body or electrically connected to the patient plate through another conducting path, a high-frequency circuit is formed through the doctor's body. This may cause the part of the doctor's body touching the conducting path to be burned.

SUMMARY OF THE INVENTION

An object of the present invention is to provide a high-frequency instrument for an endoscope that allows the doctor to perform an endoscopic high-frequency treatment with improved safety, without the danger of causing an accident resulting in a burn.

Other objects and advantages of the present invention will become apparent from the following detailed description of illustrated embodiments of the invention.

According to the present invention, there is provided a high-frequency instrument for an endoscope including an electrically insulating sheath having a high-frequency electrode provided at the distal end thereof. A operating part is connected to the proximal end of the sheath. The operating part includes an electrically conducting member electrically connected to the high-frequency electrode. The operating part further includes a connecting terminal for connection to a high-frequency power supply. An electrically insulating member covers the whole outer surface of the electrically conducting member.

In addition, there is provided a high-frequency instrument for an endoscope including an electrically insulating sheath having an electrically conductive rod inserted therein. The rod projects from the proximal end of the sheath and is electrically connected to a high-frequency electrode provided at the distal end of the sheath. A operating part is detachably connected to the proximal end of the sheath. The operating part includes an operating member disengageably engaged with the rod. An electrically insulating member covers the whole outer surface of the rod except a portion thereof that is engageable with the operating member.

BRIEF DESCRIPTION OF THE DRAWINGS

The present invention may be more fully understood from the description of preferred embodiments of the invention set forth below, together with the accompanying drawings, in which.

DESCRIPTION OF THE EMBODIMENTS

Embodiments of the present invention will be described below with reference to the accompanying drawings.

Figure 1:
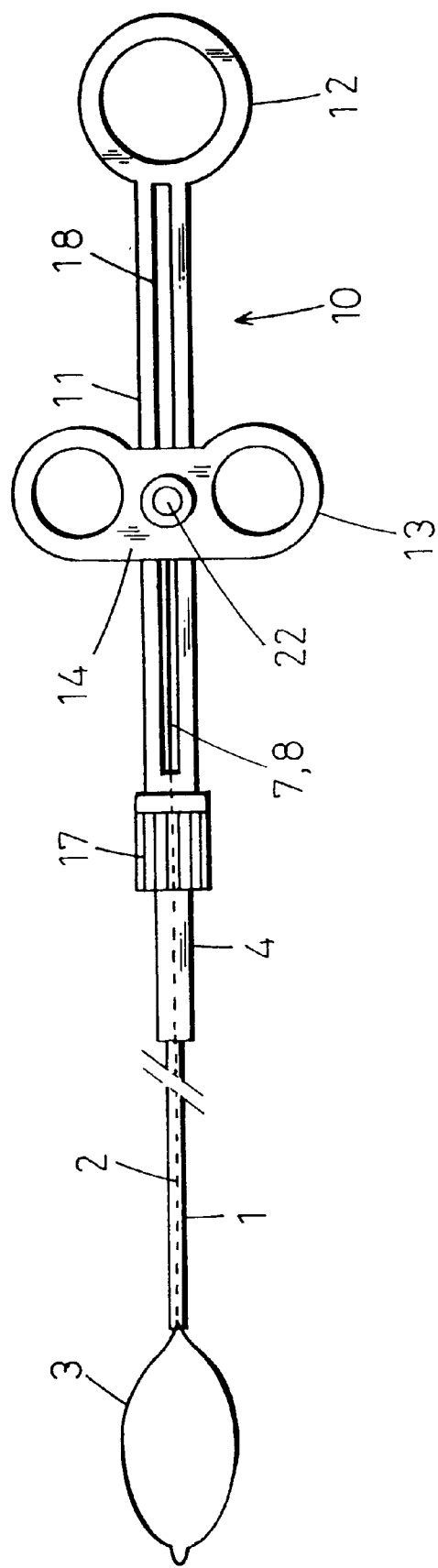
FIG. 1 is a plan view showing the whole arrangement of a high-frequency instrument for an endoscope according a first embodiment of the present invention.

FIG. 1 shows a high-frequency snare as an example of high-frequency instruments for endoscopes. A flexible sheath 1 is removably inserted into an instrument-inserting channel of an endoscope (not shown). The flexible sheath 1 is formed from an electrically insulating flexible tube, for example, a tetrafluoro-ethylene resin tube.

An electrically conductive control wire 2 is axially movably inserted in the flexible sheath 1 over the entire length thereof. An electrically conductive snare loop 3 (high-frequency electrode) is connected to the distal end of the control wire 2. In response to an operation of advancing or retracting the control wire 2, the snare loop 3 projects from or withdraws into the distal end of the flexible sheath 1 and expands or contracts by its own elasticity.

The proximal end portion of the flexible sheath 1 is covered with a buckling preventing tube 4 to prevent the proximal end portion from buckling, which might otherwise be caused by a sharp bend. It should be noted that the present invention is applicable not only to high-frequency snares but also to various high-frequency instruments for endoscopes that have a high-frequency electrode at the distal end.

A operating part 10 for advancing or retracting the control wire 2 is connected to the proximal end of the flexible sheath 1. The operating part 10 has a bar-shaped operating part body 11. A first finger engagement portion 12 for engagement with the doctor's thumb is formed at the proximal end of the operating part body 11. A second finger engagement portion 13 for engagement with the doctor's index and middle fingers is formed on a slider 14 that is slidably engaged with the operating part body 11.

Figure 2:
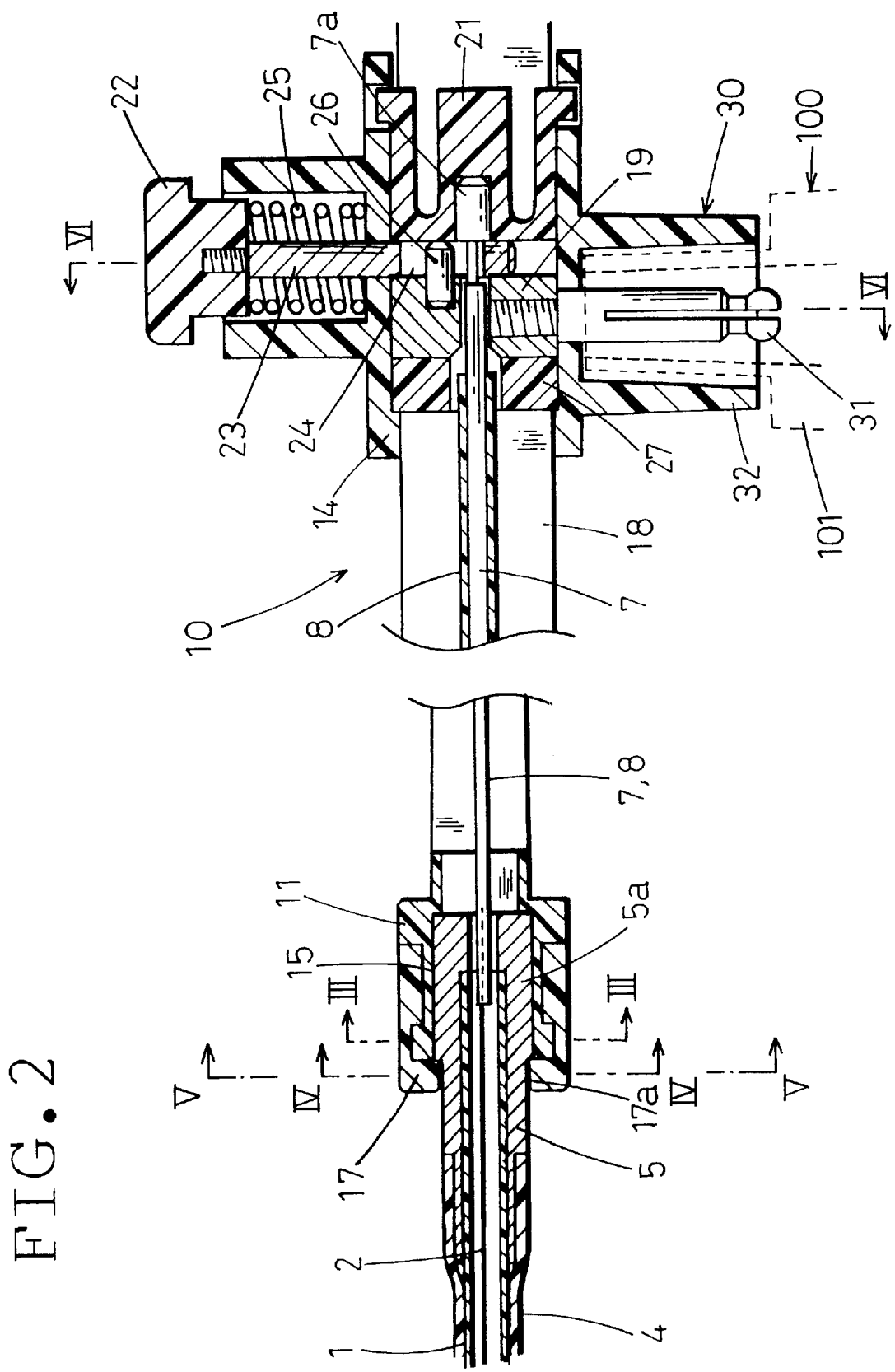
FIG. 2 is a fragmentary enlarged sectional view of a operating part of the high-frequency instrument according to the first embodiment of the present invention.

FIG. 2 is a fragmentary enlarged sectional view of the operating part 10. A proximal end cap 5 is attached to the proximal end of the flexible sheath 1. The proximal end cap 5 is inserted into a square hole 15 formed in the distal end of the operating part body 11.

The proximal end cap 5 is secured to the operating part body 11 by a connecting cylinder 17 installed on the operating part body 11. The connecting cylinder 17 surrounds the distal end portion of the operating part body 11 so as to be immovable in the axial direction but rotatable through 45 degrees, for example, about the axis of the operating part body 11.

Figure 3:
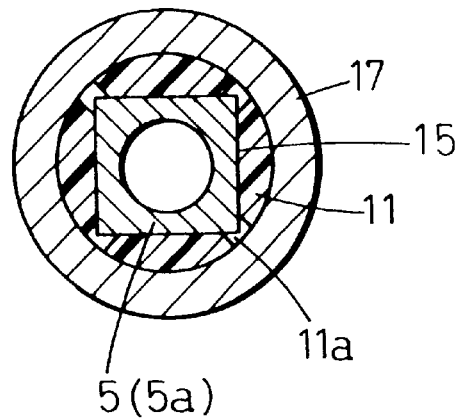
FIG. 3 is a sectional view taken along the line III—III in FIG. 2, showing the first embodiment of the present invention.

FIG. 3 is a sectional view taken along the line III—III in FIG. 2. In FIG. 3, illustration of the interior of the proximal end cap 5 is omitted. Slits 11a are formed in the distal end portion of the operating part body 11 at regular intervals of 90 degrees, for example. The slits 11a extend parallel to the axis of the operating part body 11. Therefore, the connecting cylinder 17 can be fitted onto the distal end portion of the operating part body 11 by elastically deforming the distal end portion of the operating part body 11 inwardly in a state where the proximal end cap 5 is not fitted therein.

Figure 4:
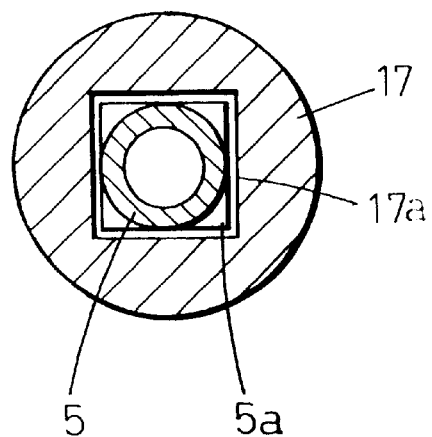
FIG. 4 is a sectional view taken along the line IV-13 IV in FIG. 2, showing a connecting cylinder in a non-locking position in the first embodiment of the present invention.

FIG. 4 is a sectional view taken along the line IV—IV in FIG. 2. As shown in FIG. 4, a square hole 17a is formed in the front end wall of the connecting cylinder 17 to pass a square shaft portion 5a of the proximal end cap 5. Through the square hole 17a, the square shaft portion 5a of the proximal end cap 5 attached to the flexible sheath 1 can be fitted into the square hole 15 formed inside the operating part body 11.

Figure 5:
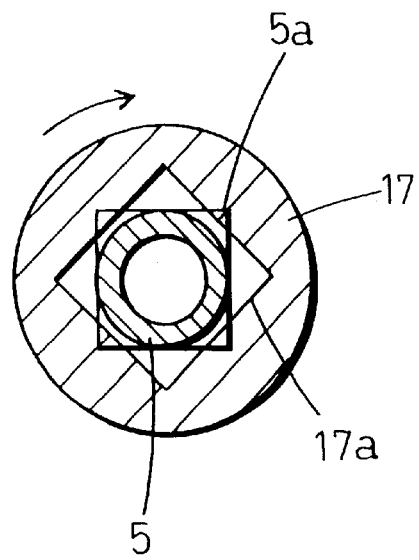
FIG. 5 is a sectional view taken along the line V—V in FIG. 2, showing the connecting cylinder in a locking position in the first embodiment of the present invention.

Consequently, the proximal end cap 5 is capable of engaging and disengaging from the operating part body 11. As shown in FIG. 5, which is a sectional view taken along the line V—V (the same as the line IV-IV) in FIG. 2, when the connecting cylinder 17 is rotated through 45 degrees, the square hole 17a of the connecting cylinder 17 is placed in a position where it does not pass the square shaft portion 5a of the proximal end cap 5. Thus, the proximal end cap 5 is held to the operating part body 11. It should be noted that in the present invention the flexible sheath 1 may be inseparably connected to the operating part 10.

Figure 6:
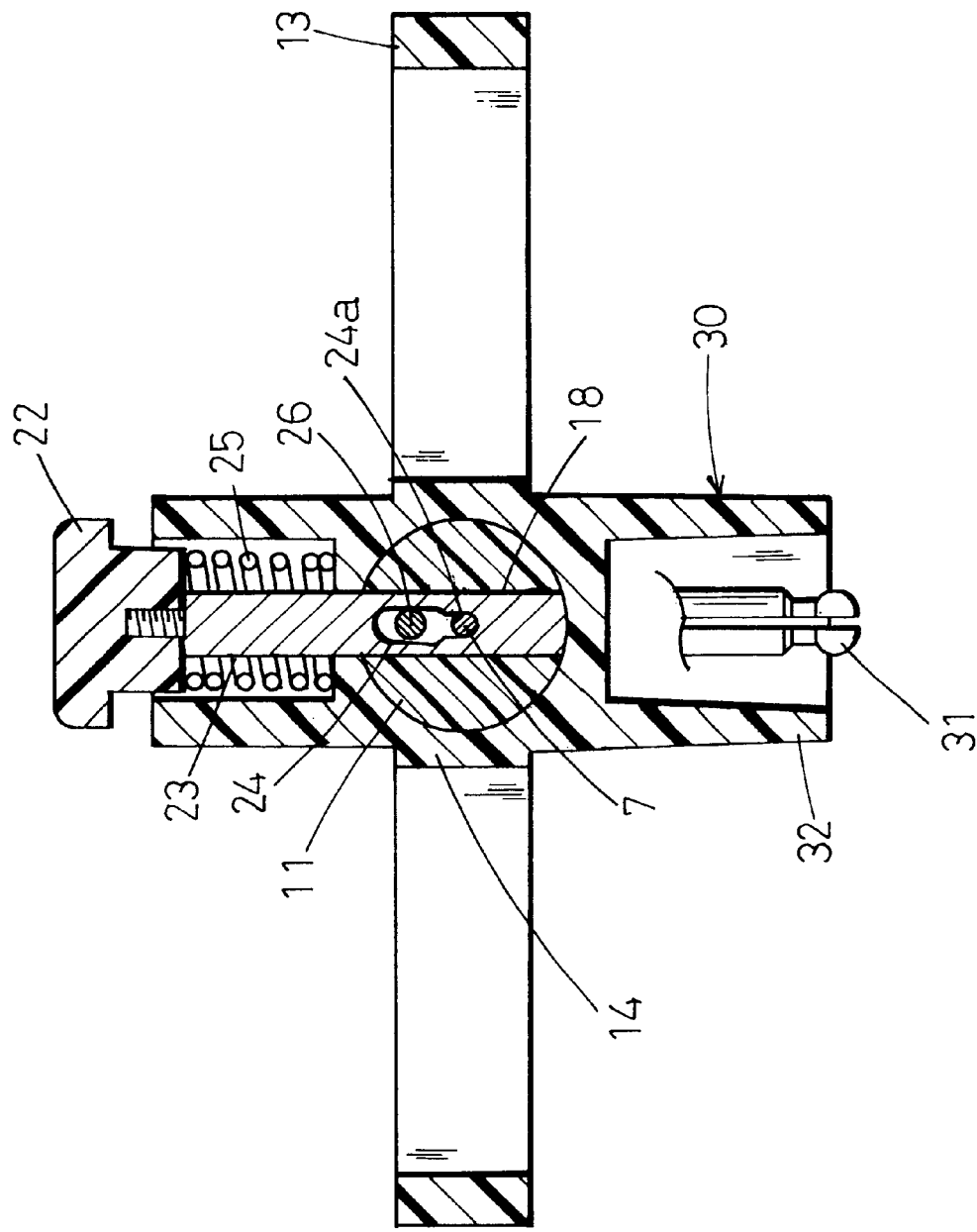
FIG. 6 is a sectional view taken along the line VI—VI in FIG. 2, showing the first embodiment of the present invention.

The right-hand half of FIG. 2 shows a part of the slider 14 that is in engagement with the operating part body 11. FIG. 6 is a sectional view taken along the line VI—VI in the right-hand half of FIG. 2.

A rod 7 is connected to the proximal end of the control wire 2, which is inserted in the flexible sheath 1, in the proximal end portion of the flexible sheath 1. The rod 7 is made of an electrically conductive metal and passed through the center of a slot 18 formed longitudinally in the operating part body 11 (i.e. the rod 7 extends along the axis of the operating part body 11).

An electrically insulating block 21 is held by the slider 14 in the slot 18. The insulating block 21 has a closed-end hole in the center thereof. A stopper 7a formed on the proximal end of the rod 7 is inserted into the closed-end hole of the insulating block 21. The stopper 7a has a larger diameter than that of the rod 7.

A lock/unlock button 22 is used to lock and unlock the stopper 7a of the rod 7 with respect to the slider 14. The lock/unlock button 22 has a slide plate 23 connected to the axial center of the lock/unlock button 22. The slide plate 23 has a slit 24 barely wide enough for the stopper 7a of the rod 7 to pass.

The lock/unlock button 22 is urged outward by a compression coil spring 25. Pressing in the lock/unlock button 22 against the urging force of the compression coil spring 25 causes the slide plate 23 to be set in a position where the stopper 7a can pass through the slit 24. Thus, the proximal end of the rod 7 can be engaged with or disengaged from the slider 14.

On release of the lock/unlock button 22, the rod 7 is set in a narrow portion 24a of the slit 24, where the stopper 7a cannot pass through the slit 24, by the urging force of the compression coil spring 25. Thus, the proximal end of the rod 7 is locked to the slider 14.

Accordingly, as the slider 14 is advanced or retracted in this state, the control wire 2 advances or retracts in the flexible sheath 1. Thus, the snare loop 3 at the distal end of the flexible sheath 1 can be remotely operated. An electrically conductive terminal-retaining member 19 has an electrically conducting pin 26 projecting therefrom so as to be engaged in the slit 24. The electrically conducting pin 26 serves as both a stopper and a guide and performs an electrically conducting function.

A high-frequency power supply connecting terminal 30 is provided on a side of the slider 14 opposite to the side on which the lock/unlock button 22 is provided. The high-frequency power supply connecting terminal 30 has a contact pin 31 and an insulating cylinder 32 integrally formed with the slider 14.

The contact pin 31 is formed of an electrically conductive metal and screwed into the terminal-retaining member 19 placed in the slot 18. When a connecting plug 100 (outlined by the dashed line) of a high-frequency power supply cord is connected to the high-frequency power supply connecting terminal 30, a high-frequency electric current can be supplied to the snare loop 3 from the contact pin 31 through the terminal-retaining member 19, the slide plate 23, the rod 7, the control wire 2, etc.

Inside the slider 14, the rear end surface of the terminal-retaining member 19, through which the high-frequency electric current flows, is covered with the above-described insulating block 21, and the front end surface of the terminal-retaining member 19 is covered with an insulating member 27 of electrically insulating properties that is secured between the terminal-retaining member 19 and a step portion formed on the slider 14.

Moreover, the rod 7 is covered with an electrically insulating tube 8, e.g. a tetrafluoroethylene resin tube, over the entire length thereof. In addition, the lock/unlock button 22, which is attached to the outer end of the slide plate 23, is made of an electrically insulating plastic material.

Furthermore, the whole outer surface of the connecting plug 100 is sheathed with a cover 101 made of an electrically insulating plastic material. When the connecting plug 100 is connected to the high-frequency power supply connecting terminal 30, the contact pin 31 cannot be touched from the outside.

Thus, when the high-frequency electric current is supplied to the snare loop 3, the outer surfaces of all the electrically conducting portions in the operating part 10 are covered with electrically insulating materials. Therefore, there is no danger of the doctor touching an electrically conducting portion. The same is the case with a second embodiment described below.

It should be noted that the insulating cylinder 32 may be omitted from the high-frequency power supply connecting terminal 30. In such a case, when the connecting plug 100 is not connected, the contact pin 31 projects from the slider 14 alone. However, when the connecting plug 100 is connected, the contact pin 31 is completely surrounded by the connecting plug 100 and cannot be touched from the outside.

Figure 7:
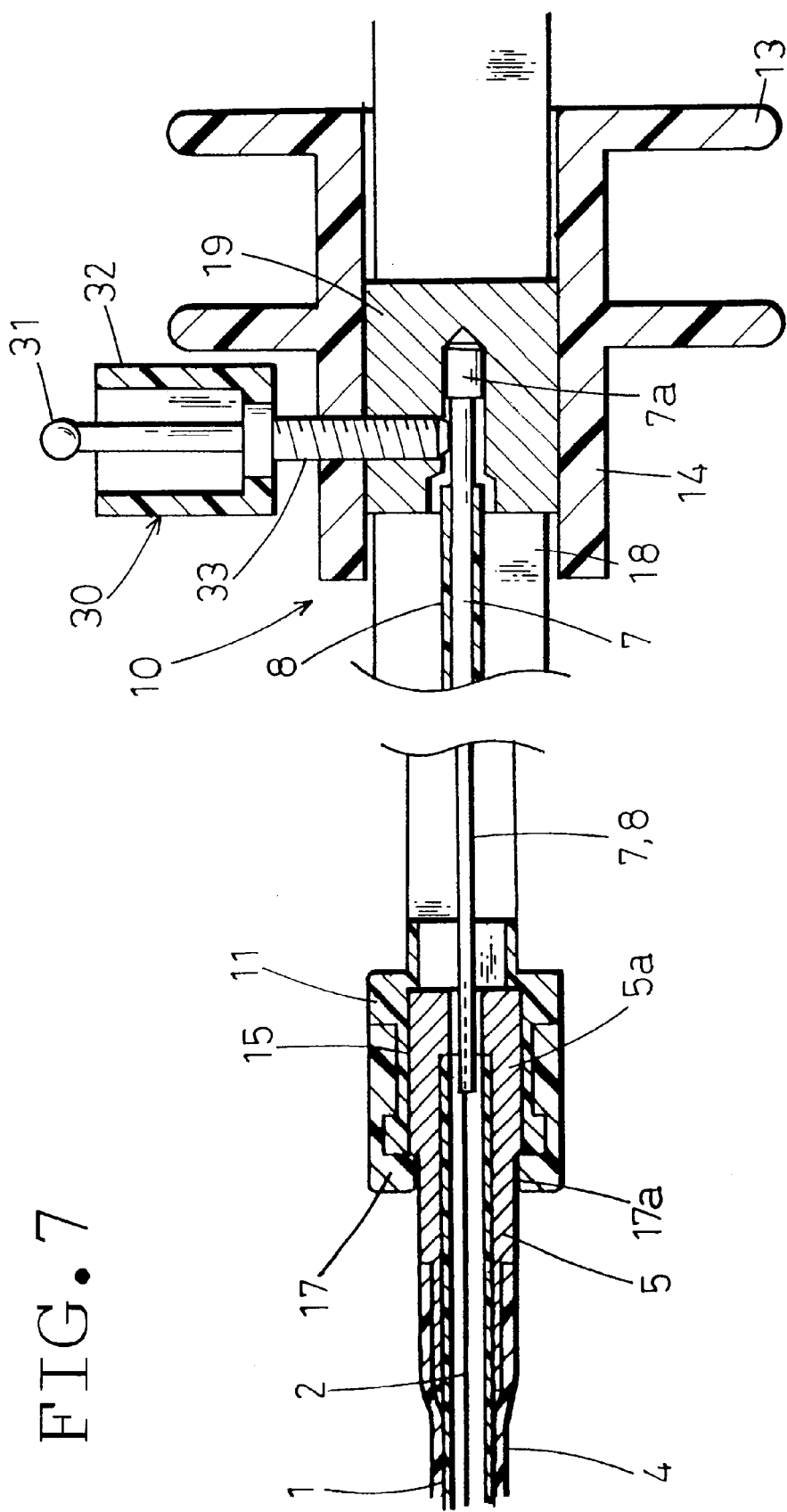
FIG. 7 is a fragmentary enlarged sectional view of a operating part of a high-frequency instrument for an endoscope according to a second embodiment of the present invention.

FIG. 7 shows a operating part 10 of a high-frequency instrument for an endoscope according to a second embodiment of the present invention. The second embodiment differs from the first embodiment only in the arrangement of a slider 14 shown in the right-hand half of FIG. 7. The arrangement of the rest of the second embodiment is the same as in the first embodiment.

A high-frequency power supply connecting terminal 30 has a contact pin 31 projecting in the center of an insulating cylinder 32. An externally threaded portion 33 is provided at the root of the high-frequency power supply connecting terminal 30. The externally threaded portion 33 is integral with the contact pin 31 and screwed into a terminal-retaining member 19 through the slider 14 from a side thereof. The distal end of the externally threaded portion 33 abuts on a portion of a rod 7 near the projecting end thereof.

When the high-frequency power supply connecting terminal 30 is turned in a direction in which the externally threaded portion 33 is unscrewed to disengage the distal end of the externally threaded portion 33 from the rod 7, the rod 7 can be pulled out from the terminal-retaining member 19. Accordingly, the lock/unlock button 22 in the first embodiment is not provided in the second embodiment.

The whole outer surface of the rod 7 is covered with an electrically insulating tube 8, e.g. a tetrafluoro-ethylene resin tube, except the portion of the rod 7 near the projecting end thereof, which is pressed by the externally threaded portion 33. The distal end of the electrically insulating tube 8 extends into the flexible sheath 1.

Accordingly, even in the case of using a pirated operating part 10 of inferior electrical safety, for example, in which the width of the slot 18 is so wide that the doctor's finger is likely to enter the slot 18, the doctor's finger cannot touch the rod 7 but may touch the electrically insulating tube 8 covering the rod 7. Therefore, there is no danger of causing an accident resulting in a burn. The same is true of the above-described first embodiment.

According to the present invention, the whole outer surface of the electrically conducting member placed in the operating part in electrical connection to the high-frequency electrode is covered with an electrically insulating member. Therefore, when a high-frequency electric current is supplied, the doctor cannot touch an electrically conducting portion in the operating part. Accordingly, there is no likelihood of the doctor causing an accident resulting in a burn when carrying out an endoscopic high-frequency treatment.

In addition, the whole outer surface of an electrically conductive rod, which is connected to the high-frequency electrode at the distal end of the sheath and projects from the proximal end of the sheath, is covered with an electrically insulating member, except a portion of the rod that is placed in the operating part and engageable with an operating member. Accordingly, when the instrument is connected to a operating part produced without giving full consideration to electrical safety, there is little likelihood of the doctor causing an accident resulting in a burn because the rod carrying a high-frequency electric current cannot directly be touched by the doctor. Thus, electrical safety can be improved.

While the invention has been described by reference to specific embodiments chosen for purposes of illustration, it should be apparent that numerous modifications could be made thereto by those skilled in the art without departing from the basic concept and scope of the invention.

What is claimed is:

1. A high-frequency instrument for an endoscope comprising:
   an electrically insulating sheath;
   a first electrically conducting member inserted in said sheath;
   a high-frequency electrode provided at a distal end of said sheath; and
   an operating part connected to a proximal end of said sheath, said operating part comprising:
   a) a second electrically conducting member electrically connected to said high-frequency electrode, wherein an entire outer surface of said second electrically conducting member is substantially covered with an electrically insulating member; and
   b) a connecting terminal for electrical connection to a high-frequency power supply, said connecting terminal comprising a connector configured to removably electrically and mechanically connect said first electrically conducting member and said second electrically conducting member; wherein said connector comprises;
   a pin; and
   a slide late having a slit, an edge of said slit configured to slidingly and electrically engage said pin.

2. The high-frequency instrument according to claim 1, wherein when a connecting plug for the high-frequency power supply is connected to said connecting terminal, at least a portion of an outer surface of said second electrically conducting member is covered with an electrically insulating member of the connecting plug.

3. The high-frequency instrument according to claim 1, wherein said sheath and said operating part are detachably connected to each other.

4. A high-frequency instrument for an endoscope comprising:
   an electrically insulating sheath;
   an electrically conductive rod inserted in said sheath, said rod projecting from a proximal end of said sheath, wherein an entire outer surface of said rod is substantially covered with an electrically insulating member;
   a high-frequency electrode provided at a distal end of said sheath, said rod electrically connected to said electrode; and
   an operating part detachably connected to said proximal end of said sheath, said operating part comprising an operating member configured to removably engage said rod, said operating member comprising a connecting terminal configured for connection to a high-frequency power supply, said connecting terminal electrically connected to said rod, said connecting terminal comprising a connector configured to removably electrically and mechanically connect said rod and said operating member; wherein said connector comprises;
   a pin; and
   a slide plate having a slit, an edge of said slit configured to slidingly and electrically engage said pin.

* * * * *